United States Patent [19]
Simmons et al.

[11] Patent Number: 5,611,776
[45] Date of Patent: Mar. 18, 1997

[54] MEANS AND METHOD FOR SEQUENTIAL ORAL ADMINISTRATION OF MULTIPLE FLUIDS TO INFANTS

[76] Inventors: Chelsey Simmons; Renee Simmons, both of 3020 NW. 9th Pl., Gainesville, Fla. 32605

[21] Appl. No.: 502,452

[22] Filed: Jul. 14, 1995

[51] Int. Cl.$^6$ .................................................. A61M 31/00
[52] U.S. Cl. .......................... 604/65; 604/73; 604/77; 604/51; 215/6; 215/11.1; 215/11.3; 215/11.4; 222/129
[58] Field of Search ........................... 604/77, 79, 65, 604/73; 606/234, 235, 236; 215/6, 11.1–11.5; 206/222; 426/115, 117, 120; 220/404, 502, 505; 222/129, 129.2, 143, 144.5, 145

[56] References Cited

U.S. PATENT DOCUMENTS

| | | | |
|---|---|---|---|
| 2,876,113 | 3/1959 | Barton | 426/117 |
| 2,885,104 | 5/1959 | Greenspan | 426/117 |
| 3,741,383 | 6/1973 | Wittwer | 426/120 |
| 4,558,792 | 12/1985 | Cabernoch et al. | 215/11.3 |
| 4,953,750 | 9/1990 | Abernathy | 220/404 |
| 4,959,051 | 9/1990 | Glass et al. | |
| 4,971,211 | 11/1990 | Lake | |
| 5,060,811 | 10/1991 | Fox | |
| 5,244,122 | 9/1993 | Botts | 215/11.1 |
| 5,269,425 | 12/1993 | Gomez-Acevedo | |
| 5,353,964 | 10/1994 | Liu et al. | |
| 5,354,274 | 10/1994 | Demeter et al. | 606/234 |
| 5,437,381 | 8/1995 | Herrmann | 215/11.1 |
| 5,456,090 | 10/1995 | McCoy | 215/11.1 |
| 5,462,526 | 10/1995 | Barney et al. | 604/82 |

Primary Examiner—Vincent Millin
Assistant Examiner—Perry E. Van Over
Attorney, Agent, or Firm—Saliwanchik, Lloyd & Saliwanchik

[57] ABSTRACT

A baby bottle for the sequential oral administration of different fluids useful in new methods for weaning an infant from one fluid to another; methods for administering medicines to an infant; and methods for putting an infant to bed with a bottle without the fear of causing premature tooth decay.

15 Claims, 3 Drawing Sheets

MEANS AND METHOD FOR SEQUENTIAL ORAL ADMINISTRATION OF MULTIPLE FLUIDS TO INFANTS

FIELD OF THE INVENTION

The present invention relates to the field of nursing bottles, and more particularly it is related to a nursing bottle which allows the sequential oral administration of multiple fluids without the need to switch bottles or manually access additional compartments.

BACKGROUND OF THE INVENTION

It is often desirable to administer two or more different liquid foods or solutions to infants in sequential order. For example, liquid medicine followed by milk, water, or fruit juice; or to provide an infant with milk and juice at mealtime. Nursing bottles are commonly used to feed babies with water, milk, juice, medicine, or any of a variety of edible nutritive fluids. A normal nursing bottle generally comprises a bottle, a nipple, and a cap fastened to the mouth of the bottle to hold the nipple in place. This structure of nursing bottle can only be used for feeding one fluid, or a mixture of fluids. Therefore, a parent or nursery may have to prepare several nursing bottles for feeding an infant with different fluids.

When attempting to administer medicine to an infant, the infant may refuse to take the medicine because of its strange or offensive taste. In order to coax an infant to take the medicine, the parent or nursery may alternatively feed the infant with milk, juice, or a sweet fluid during intervals of administration of medicine. However, it is not convenient to administer a number of different fluids to the infant in this manner. While switching from one bottle to another during the action of feeding, the infant may become frustrated and refuse to take any bottle, or the bottles may be accidentally dropped and thereby contaminated.

In an attempt to overcome some of these problems, the use of liquid containers or dispensers having more than one chamber has been attempted. Examples of multiple chambered baby bottles are illustrated in Liu et al., U.S. Pat. No. 5,353,964; Lake, U.S. Pat. No. 4,971,211; and Fox, U.S. Pat. No. 5,060,811. However, each of these discloses a bottle in which manual switching from one compartment to another is required to accomplish the sequential administration of different fluids. Thus, to effectively administer fluids by way of these bottles, the parent or nursery must constantly monitor the progress of fluid imbibing by the infant, which can be inconvenient or impractical. Another form of dual chambered bottle is disclosed in U.S. Pat. No. 5,269,425, issued to Gomez-Acevedo, wherein a plug separates different compositions contained in the separate compartments until force is applied to displace the plug. This bottle is designed for keeping substances separate until just prior to their administration to an infant, at which point the plug is removed and the substances contained in the separate compartments are mixed. Displacement by the plug is accomplished by shaking the bottle or squeezing the bottle with sufficient force to displace the plug. Although the '425 patent asserts that this bottle may be used to contain different substances which can be consumed in a separate manner without the necessity of mixing them, this bottle suffers from the same deficiencies as the others described above in that adult manual intervention is required to access the fluid in the second compartment. It is an object of the subject invention to permit the sequential administration of different fluids to an infant without such adult intervention as manually switching from one compartment to another. Access to the different compartments of the subject invention is accomplished merely by sucking action of the infant.

Doctors have long recommended against putting an infant to sleep with a bottle of milk because of the accelerated rotting of the teeth that can be encouraged by milk residue remaining in the infant's mouth once it falls asleep. The bottle of the subject invention overcomes this problem as well. Milk can be provided in the first chamber and water in a second chamber such that as an infant sucks and finishes off all milk in the first compartment, the baby will continue sucking and thereby gain access to a second compartment filled with water which then serves to rinse the milk residue from the baby's mouth. In this manner, the infant can be put to bed with a bottle according to the subject invention without fear of accelerating dental decay.

With the above and other objects in view, the present invention consists of the combination and arrangement of parts hereinafter more fully described. Illustrated in the accompanying drawings, and more particularly pointed out in the appended claims, it being understood that changes may be made in the form, size, proportions, and minor details of construction without departing from the spirit or sacrificing any of the advantages of the invention.

DETAILED DESCRIPTION

Figure 1:
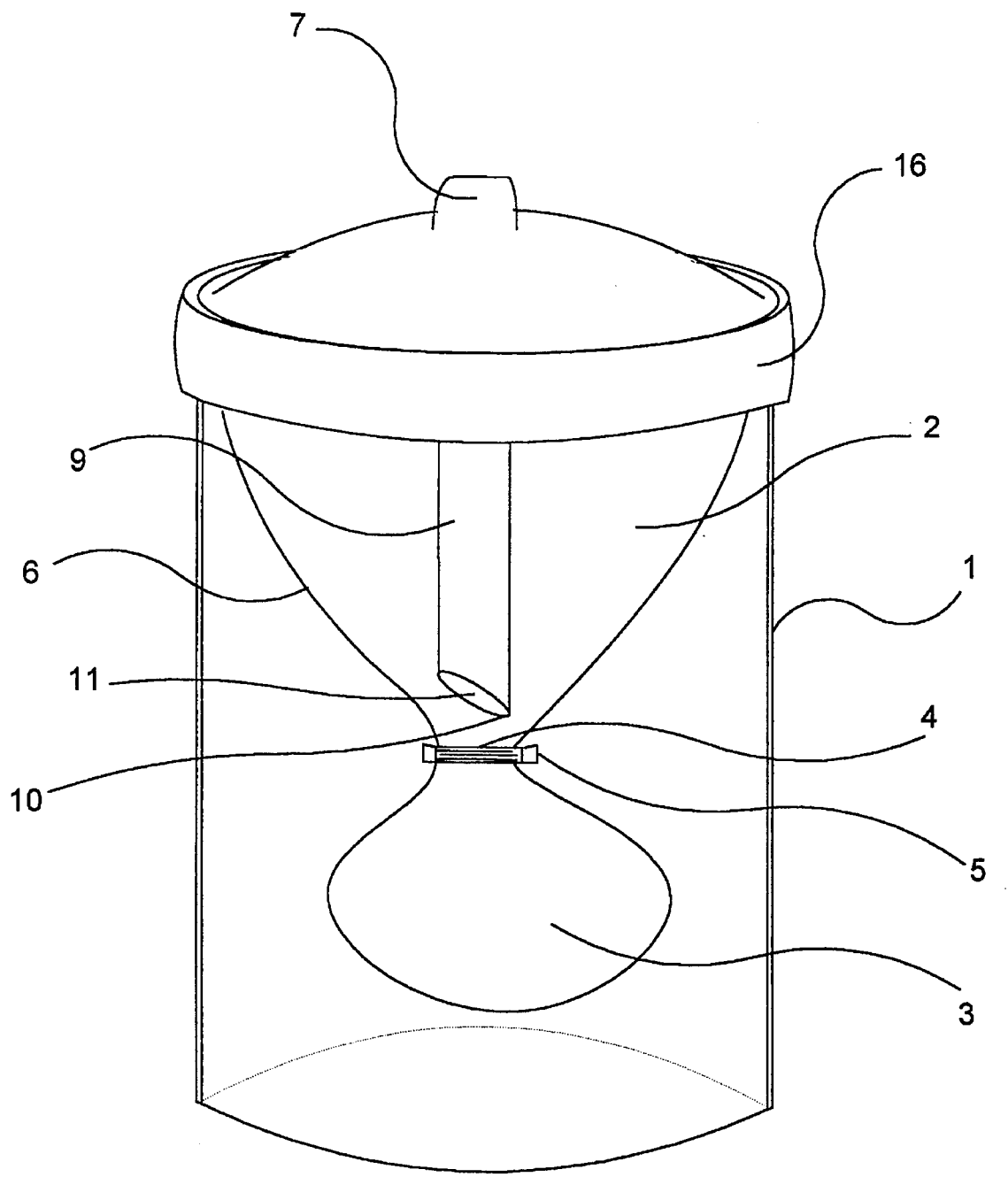
FIG. 1 depicts a preferred embodiment of the bottle of the subject invention.
Figure 2:
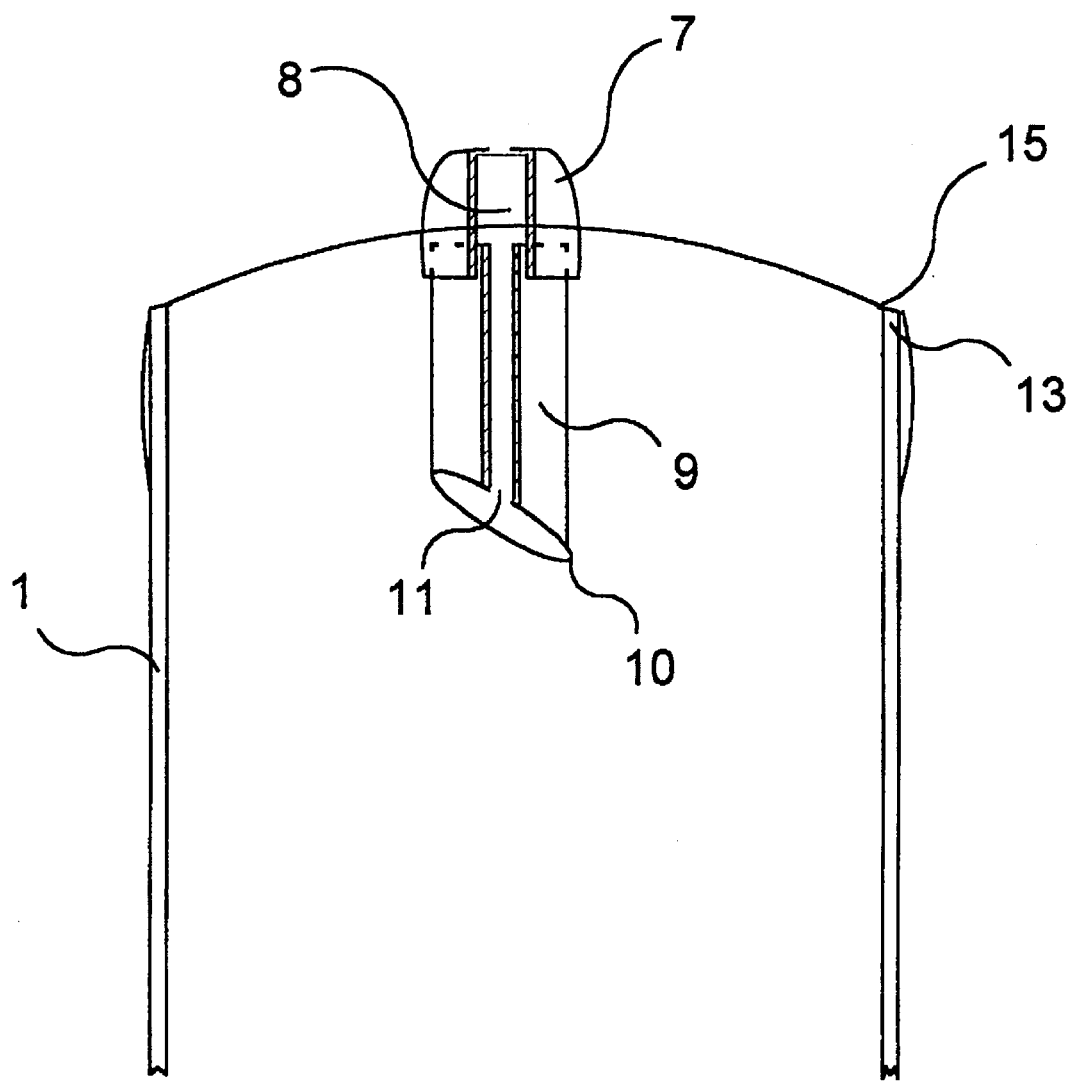
FIG. 2 is a partial cross-sectional view of an embodiment of the nipple and compartment access means.

Having now more particular reference to the drawings, and in particular with reference to FIG. 1, there is shown a nursing bottle that is built in accordance with a specific preferred embodiment of the present invention. This embodiment generally comprises a container system having at least two compartments, generally an upper compartment 2 and a lower compartment 3, effectively stacked one on top of the other and separated by a compartment barrier 4 which substantially prevents mixture of substances contained in each of the compartments. The compartments may be of the same size, or of different sizes. If of different sizes, any of the compartments may be the larger and any may be the smaller, depending on the wishes of the person using the subject invention. In the preferred embodiment depicted in FIG. 1, the compartment barrier is created by application of an external constriction means 5, for example an elastic band, to the external surface of a bag 6. Alternatively, other devices can serve as constriction means, for example, various clips, rings, ties, releasable straps, or malleable closure devices (such as wire-reinforced plastic, bendable metal, or the like), so long as they have the characteristic of allowing the constriction to be released when sufficient pressure is applied internally from within the bag at the constriction point. Alternatively, the compartment barrier may constitute an integral portion of the bag created by manufacturing techniques well known in the art for the prepackaging of fluids, thereby eliminating the need for constriction means. The bottle also comprises a nipple 7 with a sealing flange 15, a nipple compartment 8 defined by the nipple 7, a cap 16 for tightening and holding the nipple 7 in sealed engagement with the bag 6, and a compartment access means 9 in fluid connection with said nipple compartment 8 such that suction applied through the nipple 7 also creates suction within compartment access means 9, which serves to draw fluid out of the upper compartment 2 of bag 6, up through compartment access means 9, through the nipple 7, and into the mouth of whomever is applying the suction force. The nipple 7 and compartment access means 9 are shown in combination in FIG. 2.

As fluid is drawn out of the upper compartment 2, the bag 6 tends to collapse inward and upward toward the nipple 7. As suction continues to be applied, this force causes sufficient motion of the bag 6 to bring the compartment barrier 4 into contact with the penetration tip 10 of the compartment access means 9. In the preferred embodiment, the penetration tip 10 is appropriately configured so as to breach the compartment barrier 4 by wedging its way through the barrier as the suction force pulls the bag 6 upwards against the penetration tip 10. Once the compartment barrier 4 has been breached, an accession orifice 11 of the compartment access means 9 gains access to the lower compartment 3, and the fluid contained therein may be drawn into the accession orifice 11, up through the compartment access means 9, and out of the nipple 7 into the mouth of whomever is applying the suction force.

Assembly of the subject invention generally comprises introducing a first fluid into the lower compartment 3, by pouring it into the open end of the bag 6. Once the desired amount of fluid has been introduced, the constriction means 5 is externally applied to the bag 6 thereby creating a compartment barrier 4, and a lower compartment 3 (now filled) and an upper compartment 2 (still empty). Alternatively, if the bag has an integral compartment barrier, then presumably a fluid has already been introduced and contained in the lower compartment as part of the manufacturing process. Such prepackaging technology is well-known in the art and has been used for prepackaging of milk, juices, and various other fluids.

A second fluid may now be introduced through the open end of the bag 6 into the upper compartment 2. Once the desired amount of the second fluid has been introduced into the upper compartment 2, the nipple 7 and the compartment access means 9 combination is lowered into place such that the nipple sealing flange 15 rests on the top rim 13 of the container 1 and the compartment access means 9 extends down into the upper compartment 2 to a sufficient extent to contact the fluid therein. The nipple and compartment access means combination has been secured in place by application of the cap 16 to the container 1 by means well-known in the art. Once so assembled, the bottle is ready for use.

Figure 3:
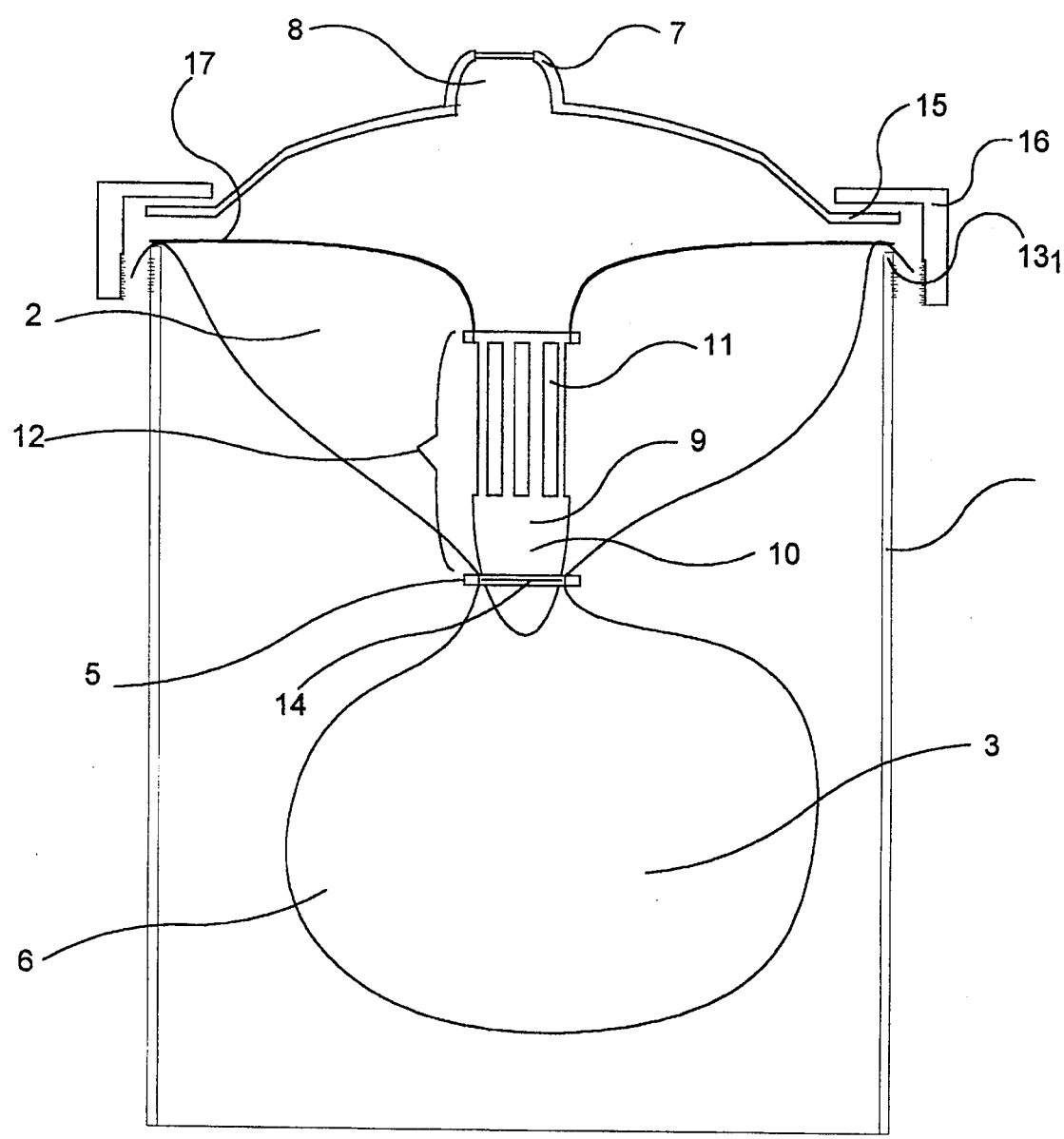
FIG. 3 depicts a partial sectional view of an alternative embodiment of the compartment access means in the assembled bottle configuration.

An alternative embodiment of the compartment access means 9 is more clearly depicted in FIG. 3. Whereas the first embodiment of the compartment access means described herein comprises an orifice disposed at the penetration tip, this alternative embodiment has at least one orifice 11 positioned on the penetration shaft 12 above the penetration tip 10, and has a sealing flange 17, as well. In this configuration, the bottle is assembled by placing the bag 6 in the container 1, and introducing a first fluid into the open end of the bag. Once the desired amount of this first fluid has been introduced, the compartment access means 9 is lowered into place atop the rim 13 of the container 1 such that the penetration tip 10 of the compartment access means extends downward into contact with the first fluid. The external constriction means 5 is then applied to the bag 6 such that the bag 6 is constricted into contact with a compartment barrier contact point 14 on the external surface of the compartment access means 9, thereby creating a substantially fluid-tight compartment barrier. A second fluid is then introduced through the open top of the compartment access means 9, and flows out of the orifice or orifices 11 of the compartment access means 9 and into the upper compartment 2 of the bag 6. Once the desired amount of the second fluid has been introduced, the nipple 7 is placed on top of the compartment access means 9 and is secured into place creating a fluid-tight seal by arrangement of the cap 16.

In operation of this embodiment, as suction is applied through the nipple 7, the fluid in the upper compartment 2 is drawn through the at least one orifice 11 of the compartment access means 9, out the nipple 7, and into the mouth of whomever is applying the suction force. As fluid is drawn from the upper compartment 2, the bag 6 tends to move inward and upward. As the bag 6 moves upward, the compartment barrier contact point 14 moves upward along the external surface of the penetration shaft 12 of the compartment access means 9. As the fluid continues to be removed from the upper compartment 2, the compartment barrier contact point 14 slides upward to sufficiently to encounter the at least one accession orifice 11, which is/are of sufficient length and configuration so as to not be completely closed off by the bag 6 at the compartment barrier contact point 14. When the bag 6 has moved sufficiently upward, the compartment barrier contact point 14 has moved above the bottom of the accession orifice 11, thereby exposing the accession orifice 11 to the fluid in the lower compartment 3 and providing whomever is applying suction with access to the fluid contained therein. As the suction applier of the bottle continues to apply suction through the nipple 7, fluid in the lower compartment 3 is drawn through the accession orifice 11, up the compartment access means 9, though the nipple 7, and into the mouth of whomever is applying suction.

The bottle of the subject invention may be conveniently constructed out of materials well-known in the art for such purposes, for example, various types of plastics and rubber which are well-known in the industry. The compartment access means is preferably made of a hard plastic having a relatively lubricous surface so as to minimize friction of the compartment barrier along the external surface thereof, but also has sufficient rigidity to breach the compartment barrier and resist the compressive force of the external constriction device. The manipulation and molding of such plastics and rubbers is well-known in the art, for example, by means such as injection molding.

The subject invention can be used to introduce new fluids to an infant, for example, by filling the lower compartment with a fluid familiar to the infant and placing a little of the new fluid to which the infant is to be introduced in the upper compartment. The infant will drink through the new fluid to get to the familiar fluid contained in the lower compartment. In this way an infant may also be weaned from one fluid to another by gradually increasing the amount of the new desired fluid and gradually decreasing the amount of fluid from which the infant is to be weaned.

An infant may be put to bed with milk without fear of causing premature tooth decay by filling the lower compartment with water and the upper compartment with milk. The infant will drink the milk, and continue sucking once the milk has been depleted, thereby accessing the water compartment and rinsing its teeth by drinking the water from the lower compartment.

The subject invention can also be used to administer medicines or other foul-tasting fluids to an infant by placing the indicated amount of medicine in the lower compartment and favored fluid in the upper compartment. The infant will drink through the favored fluid and into the medicine, which will be gone by the time the infant realizes it has switched from a favored fluid to medicine. In an alternative embodiment, the bag may be provided with multiple chambers, for example, three chambers, wherein the lowest compartment contains a favored fluid, the middle compartment contains medicine, and the upper compartment is filled with favored fluid. In operation, the infant would drink through the first compartment of favored fluid, then encounter the medicine, then finally wash the medicine down with the favored fluid from the lowest compartment.

As it will be clearly apparent from the above descriptions, the construction and use of the nursing bottle is very simple and economical. It must be understood that the embodiments of the invention described above are merely illustrative, but not limitative, of the present invention. The nursing bottle may be modified in the details thereof such as for instance modifying the number of orifices in the compartment access means, altering the angle of the compartment accession tip, or providing the bag with more than two adjacent compartments.

Although certain embodiments of the invention have been shown and described above, it is to be understood that many modifications thereof are possible. The present invention, therefore, is not to be restricted except in so far as is necessitated by the prior art and by the spirit of the appended claims.

We claim:

1. A nursing bottle for the sequential oral administration of different fluids, comprising a rigid container having an open upper end, a bag to be disposed in said container and having an open end arranged proximal to the upper end of said container, a cap having a central opening, a nipple having a sealing flange and defining a nipple compartment, said nipple being arranged in said cap so that it projects outwardly of the central opening of said cap, a compartment access means in fluid connection with said nipple compartment and comprising an accession orifice a plurality of compartments within said bag, comprising at least one upper compartment and at least one lower compartment, said compartments being separated by a breachable compartment barrier and configured such that when sufficient suction force is applied on said nipple and through said compartment access means, said compartment barrier is brought into contact with said compartment access means and is thereby breached.

2. The nursing bottle of claim 1, further comprising constriction means, said constriction means disposed on the external surface of said bag so as to create said compartment barrier.

3. The nursing bottle of claim 2, wherein said constriction means is an elastic band.

4. The nursing bottle of claim 2, wherein said constriction means is a clip.

5. The nursing bottle of claim 2, wherein said constriction means is a releasable strap.

6. The nursing bottle of claim 2, wherein said constriction means comprises a tie.

7. The nursing bottle of claim 2, wherein said constriction means is a ring.

8. The nursing bottle of claim 2, wherein said constriction means is a malleable closure device.

9. The nursing bottle of claim 1, wherein said breachable compartment barrier is an integral part of said bag.

10. A method for the sequential oral administration of different fluids comprising the steps of providing a bottle comprising a bag having at least one lower compartment and at least one upper compartment, said compartments being separated by a breachable compartment barrier and said lower compartment being filled with a first fluid; introducing into said at least one upper compartment a fluid different from said first fluid; and giving the bottle to a person to whom the different fluids are to be administered.

11. The method of claim 10, wherein one of said fluids is milk and another of said fluids is water.

12. The method of claim 10, wherein one of said fluids is medicine and another of said fluids is selected from the group consisting of milk, juice, or water.

13. A method for the sequential oral administration of different fluids comprising the steps of providing a bottle according to claim 1, wherein said lower compartment contains a first fluid and said upper compartment contains a second fluid different from said first fluid; and giving the bottle to a person to whom the different fluids are to be administered.

14. The method of claim 13, wherein one of said fluids is milk and another of said fluids is water.

15. The method of claim 13, wherein one of said fluids is medicine and another of said fluids is selected from the group consisting of milk, juice, or water.

* * * * *